United States Patent [19]

Baran et al.

[11] Patent Number: 5,137,904
[45] Date of Patent: Aug. 11, 1992

[54] THIOHYDANTOIN INHIBITORS OF COLLAGEN-INDUCED AND ADP-INDUCED PLATELET AGGREGATION

[75] Inventors: John S. Baran, Winnetka; Tom Lindberg, Wheaton; Robert H. Mazur, Chicago, all of Ill.; Alan E. Moorman, Fort Collins, Colo.; Doug Steinman, Morton Grove, Ill.

[73] Assignee: G. D. Searle & Co., Chicago, Ill.

[21] Appl. No.: 359,003

[22] Filed: May 30, 1989

[51] Int. Cl.$^5$ .................. A61K 31/415; C07D 233/00
[52] U.S. Cl. ..................................... 514/389; 548/313; 548/312; 514/391
[58] Field of Search ................ 548/313, 312; 514/389, 514/391

[56] References Cited

FOREIGN PATENT DOCUMENTS 2259  3/1984  European Pat. Off. .
1965921 11/1969  Fed. Rep. of Germany .
52-100469  2/1976  Japan .
52-100470  2/1976  Japan .

OTHER PUBLICATIONS

Kent, et al. A study of the Edman degradation in the assessment of the purity of synthetic peptides. (Proceedings of the International Conference) 4th, 1981; pp. 205–213.

Matsueda, et al. Quantitative solid-phase Edman degradation for evaluation of extended solid-phase peptide synthesis. Biochemistry, 1981, pp. 2571–2580.

Rochat, et al. S-L Alkyl derivatives of cysteine suitable for sequenced determination by the phenylisothiocyanate technique. Anal. Biochem. 1970, 37(2), 259–67.

Steinman, et al. Synthesis of side chain-protected amino acid phenylthiohydantoins and their use in quantitative solid-phase Edman degradation. Anal. Biochem. 1985, 145(1), 91–5.

Tschesche, et al. Mass spectral identification and quantification of phenylthiohydantoin derivatives from Edman degradation or proteins. FEBS letters, 1972, 23(3), 367–72.

Hopp, Thomas. Identification of aqueous phase amino acid phenylthiohydantoins on polyamide sheets. Anal. Biochem. 1976, 74(2), 638–40.

Mak, et al. Application of S-pyridylethylato in of cysteine to the sequence analysis of proteins. Anal. Biochem. 1978, 84(2), 432–40.

Primary Examiner—Mary C. Lee
Assistant Examiner—Robert C. Whittenbaugh
Attorney, Agent, or Firm—Joy Ann Serauskas; Paul D. Matukaitis

[57] ABSTRACT

A series of ethers and thioethers of 5-methanol thiohydantoins, unsubstituted at the number one position heterocyclic nitrogen atom of the thiohydantoin ring, useful in reversing the effects of collagen and ADP-induced platelet aggregation.

23 Claims, No Drawings

THIOHYDANTOIN INHIBITORS OF COLLAGEN-INDUCED AND ADP-INDUCED PLATELET AGGREGATION

BACKGROUND OF THE INVENTION

The present invention provides novel compounds, novel compositions, methods of their use and methods of their manufacture, such compounds being pharmacologically useful in the prevention of collagen-induced or ADP-induced platelet aggregation in a mammal and in the treatment of atherosclerosis and thrombosis. More specifically, the compounds of the present invention comprise a class of ethers and thioethers of 5-methanol thiohydantoins that are unsubstituted at the No. 1 heterocyclic nitrogen atom of the thiohydantoin ring.

FIELD OF THE INVENTION

Mammalian blood cells can broadly be classified as erythrocytes, leukocytes, or platelets. The main function of platelets is to initiate the hemostatic process. They do this initially by forming a hemostatic plug at the site of a vascular injury and secondly by promoting efficient coagulation at such a site, which consolidates the plug with strands of fibrin. Platelets ordinarily circulating in the blood do not readily adhere to any surface, which is essential for the maintenance of normal blood flow. When activated, however, platelets readily adhere to each other to form an aggregate, or they adhere to the subendothelial components of the blood vessel wall that become exposed when the vascular endothelium is damaged. Platelets adhering to the subendothelium at a point of vascular damage secrete constituents that activate other platelets flowing past the damaged area. These activated platelets then form an aggregate on the adherent layer and initiate the development of a hemostatic plug or thrombus. Platelet aggregation can be induced by a variety of soluble stimuli, each interacting with a discrete receptor on the surface of the platelet. These stimuli can include adenosinediphosphate (ADP), catecholamines, certain prostaglandins, thrombin, immune complexes, complement components and collagen.

When platelets adhere to a damaged blood vessel wall, through their affinity for subendothelial collagen, then more platelets accumulate on the initial adherent layer (aggregation), a process which is brought about by the secretion from the initial adherent platelets of constituents such as ADP, arachidonate metabolites and serotonin, which in turn activate more platelets in the immediate vicinity. Calcium ions and fibrinogen, which are important co-factors in platelet aggregation, are also secreted, and the thrombin generated during the coagulation process is a powerful platelet stimulant as well as catalyzing the polymerization of fibrinogen to fibrin.

The two conditions mainly responsible for occlusive vascular disease are atherosclerosis and thrombosis. Atherosclerosis is characterized by focal lesions of the arterial intima that consist of plaques containing varying amounts of fibrous tissue and lipid. The result of plaque formation is a localized thickening of the arterial wall with subsequent narrowing of the vascular lumen. Platelets have the potential to contribute to this pathological process by secreting constituents that increase vascular permeability and induce smooth muscle proliferation in the arterial wall, and also by foreign mural thrombi that can become covered by endothelium and thus be incorporated into the arterial wall.

Drugs intended to reduce platelet activity have been administered in the hope that this may be a useful method of prophylaxis against some thrombotic conditions, and possibly against the development of atherosclerosis, as well.

Currently, anti-platelet drugs fall into three main classes: first, those that antagonize the platelet response to a specific stimulus by blocking the interaction of the stimulant with its receptor; secondly, those that prevent secondary aggregation by interfering with the secretion of constituents such as thromboxane, that induce the secondary aggregation response; and, finally, agents that decrease platelet responsiveness in general by interfering with the chain of intracellular events leading to platelet activation.

Examples of Class 1 anti-platelet drugs include phentolamine, which blocks aggregation induced by catecholamines; methysergide, which blocks serotonin; and ATP, which blocks platelet ADP. Also, compounds now exist that can specifically antagonize thromboxane-induced platelet aggregation, as well as other compounds which can specifically antagonize platelet activating factor, PAF.

Examples of Class 2 anti-platelet drugs are aspirin, which irreversibly acetylates, thereby blocking, the cyclooxygenase that converts arachidonate to the prostaglandin endoperoxides $PGG_2$ and $PGH_2$. This inability to convert arachidonate results in a inability by the platelet to aggregate in response to low concentrations of collagen.

Some class 3 platelet-inhibiting drugs are stimulators of adenylate cyclase, such as prostaglandin $E_1$, prostacyclin, prostaglandin $D_2$, and adenosine. Other Class 3 platelet inhibitors are inhibitors of phosphodiesterase such as papaverine, and certain methylxanthines (e.g., caffeine, theophylline and theobromine). Still other Category 3 platelet inhibitors are lipophilic amines with local anesthetic activity, such as procaine, chlorpromazine, amitriptylene and diphenhydramine.

Class 2 anti-platelet drugs have the disadvantage of inhibiting platelet function permanently. Since the life span of a platelet is 7-10 days, this means that certain platelet functions will be inhibited for several days to a clinically undesirable degree.

Class 3 platelet inhibitors, which ultimately exert their inhibitory effect on platelets by elevating cyclic AMP levels, tend to affect many other systems within the body, since cyclic AMP is a ubiquitous intracellular messenger, a phenomena which limits potential clinical value of Class 3 anti-platelet drugs as anti-thrombotic agents.

It is an object of the present invention to provide a class of compounds which, when administered to a mammal, inhibit the platelet aggregation effects of exposure of platelets to collagen, without affecting a multitude of other biochemical pathways within the body and without exerting a permanent effect on platelets, so as to provide a clinically useful anti-thrombotic agent. The present invention provides new ether and thioether thiohydantoin compounds which are non-substituted at the No. 1 nitrogen atom of the heterocyclic ring, and which show efficacy as anti platelet agents by virtue of their ability to inhibit platelet aggregation following platelet exposure to collagen or ADP, which are known platelet aggregation inducers.

SUMMARY OF THE INVENTION

The invention relates to novel compounds of the general formula I:

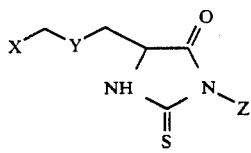

and the pharmaceutically acceptable salts thereof and the enantiomers thereof, wherein X is phenyl, halogen substituted phenyl, alkyl of 1 to 5 carbon atoms, alkenyl of 1 to 5 carbon atoms with one or more degrees of unsaturation or alkynyl of 1 to 5 carbon atoms with one or more degrees of unsaturation;

Y is O or S; and

Z is alkyl of from 1 to 5 carbon atoms, phenyl alkyl of 1 to 5 carbon atoms, phenyl or phenyl substituted by halogen, alkyl of 1 to 5 carbon atoms, alkyloxy of 1 to 5 carbon atoms, or halogen substituted alkyl of 1 to 5 carbon atoms.

The compounds and pharmaceutical compositions thereof are useful in the anti-platelet and anti-thrombotic methods of the invention.

DETAILED DESCRIPTION OF THE INVENTION

As used herein, the expressions "alkyl", "alkenyl", "alkynyl" and "alkyloxy" are defined to include straight or branched carbon-carbon linkages of 1 to 5 carbon atoms.

The term "pharmaceutically acceptable salts" refers to non-toxic salts of the compounds of this invention which are generally prepared by reacting the free base with a suitable organic or inorganic acid. Representative salts include the following salts:

Acetate Lactobionate
Benzenesulfonate Laurate
Benzoate Malate
Bicarbonate Maleate
Bisulfate Mandelate
Bitartrate Mesylate
Borate Methylbromide
Bromide Methylnitrate
Calcium edetate Methylsulfate
Camsylate Mucate
Carbonate Napsylate
Chloride Nitrate
Clavulanate Oleate
Citrate Oxalate
Dihydrochloride Pamoate (Embonate)
Edetate Palmitate
Edisylate Pantothenate
Estolate Phosphate/diphosphate
Esylate Polygalacturonate
Fumarate Salicylate
Gluceptate Stearate
Gluconate Subacetate
Glutamate Succinate
Glycollylarsanilate Sulfate
Hexylresorcinate Tannate
Hydrabamine Tartrate
Hydrobromide Teoclate
Hydrochloride Tosylate
Hydroxynaphthoate Triethiodide
Iodide Valerate
Isethionate
Lactate As used herein, the term "anti-thrombotic" shall mean the ability to suppress platelet function.

Most especially preferred compounds of the present invention are those which are namely:

3-phenyl-5-[(2-propenylthio)methyl]-2-thioxo-4-imidazolidinone;

3 -phenyl-5-[(phenylmethoxy)methyl]-2-thioxo-4-imidazolidinone;

3 -phenyl-5-[[(phenylmethyl)thio]methyl]-2-thioxo-4-imidazolidinone;

3-phenyl-5S-[[(phenylmethyl)thio]methyl]-2 -thioxo-4-imidazolidinone

3 -(phenylmethyl-5-[[(phenylmethyl)thio]methyl]-2-thioxo-4-imidazolidinone;

3-ethyl-5-[[(phenylmethyl)thio]methyl]-2-thioxo-4-imidazolidinone;

3-(4 -methylphenyl)-5-[[(phenylmethyl)thio]methyl]-2-thioxo-4-imidazolidinone;

3 -(4-chlorophenyl)-5-[[(phenylmethyl)thio]methyl]-2-thioxo-4-imidazolidinone;

3-(3-chlorophenyl-5 [[(phenylmethyl)thio]methyl]-2-thioxo-4-imidazolidinone;

5-[[[(4 -chlorophenyl)methyl]thio]methyl]-3 -phenyl-2-thioxo-4-imidazolidinone 3-(4-methoxyphenyl)-5 [[(phenylmethyl)thio]methyl]-2-thioxo-4-imidazolidinone; and 5-[[(phenylmethyl)thio]methyl]-2 -thioxo-3 -[(3-trifluoromethyl)phenyl]-4-imidazolidinone.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned here in greater detail.

SCHEME 1

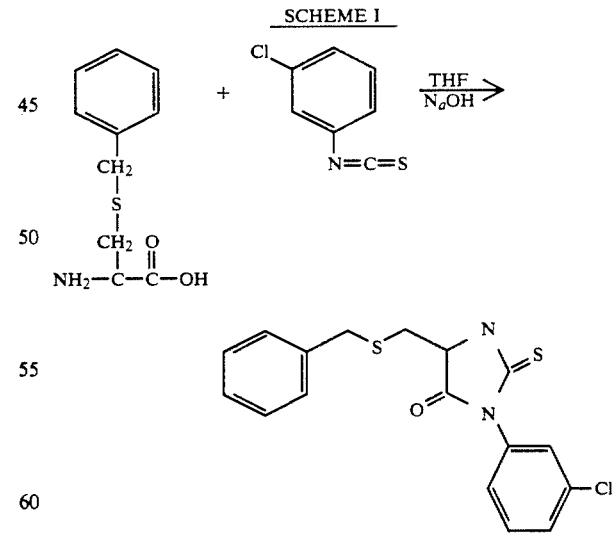

The compounds of the present invention can be administered in such oral dosage forms as tablets, capsules, pills, powders, granules, elixirs, tinctures, suspensions, syrups and emulsions. Likewise, they may also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed as an anti-thrombotic agent in the inhibition of aggregation of platelets. The dosage regimen utilizing the compounds of the present invention is selected in accordance with a variety of factors including the type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, treat or arrest the progress of the condition.

Dosages of the compounds of the present invention, when used for the indicated effects, will range between about 0.1 mg/kg of body weight per day (mg/kg/day) to about 1,000 mg/kg/day and preferably 1.0–100 mg/kg/day. Advantageously, the compound of the present invention may be administered in a single daily dose or the total daily dosage may be administered in divided doses of 2, 3 or 4 times daily.

Furthermore, preferred compounds of the present invention may also be administered in intranasal form topically via the use of suitable intranasal vehicles, or via transdermal routes, using those forms of transdermal skin patches well known to those of ordinary skill in that art or by lotions, shampoos, creams, ointments or gels. If administered in the form of a transdermal delivery system, then dosage administration will, of course, be continuous throughout the dosage regimen.

In the method of the present invention, the foregoing compounds described in detail above can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral non-toxic pharmaceutically acceptable inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugar such as glucose or beta-lactose, corn sweeteners, natural and synthetic gums such as acacia, tragacanth or sodium alginate, carboxy methyl cellulose, polyethylene glycol, waxes and the like. Lubricants for use in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholine.

The compounds of the present invention may also be delivered by the use of monoclonal antibodies as individual carriers to which the compound molecules are coupled. The compounds of the present invention may also be coupled with soluble polymers as targetable drug carriers. Such polymers may include polyvinylpyrrolidone, pyran copolymer, polyhydroxypropylmethacrylamide-phenol, polyhydroxyethylaspartimide phenol, or polyethyleneoxide- polylysine substituted with palmitoyl residues. Furthermore, the compounds of the present invention may be coupled to a class of biodegradable polymers useful in achieving controlled release of drug, for example, polylactic acid, polyglycolic acid, copolymers of polylactic and polyglycolic acid, polyepsiloncaprolactone, polyhydroxybutyric acid, polyorthoesters, polyacetals, polydihydropyrans, polycyanoacrylates and cross-linked or amphipathic block copolymers of hydrogels.

The compounds of this invention exhibit anti-platelet activity to the extent that they inhibit aggregation of platelets exposed to collagen or ADP and are useful as anti- thrombotic agents.

Our present understanding would suggest that when the vascular endothelium is sufficiently damaged, collagen is exposed. Platelets rapidly adhere and undergo the release reactions described previously. Following the release of platelet granule contents, especially ADP, other platelets are then stimulated to aggregate and a hemostatic plug is formed at the site of vascular damage. The test procedures employed to measure anti aggregation activity of the compounds of the present invention are described below.

EXAMPLE 1

Test 1

5 $\mu$M ADP (adenosinediphosphate) is added in vitro to 50 $\mu$L of vehicle and 400 $\mu$L of platelet-rich plasma of humans from either sex who have not taken any non-steroidal anti-inflammatory drugs for ten days prior to blood-letting. After an ADP-induced platelet aggregation response is seen, 50 $\mu$L of compound is incubated with the aggregated platelets for ninety seconds at 37° C. A compound is rated active if, after three separate incubations, the mean ADP-induced response is reduced by 50% or more.

A suitable vehicle for drug delivery in this test is 0.154M NaCl, 19.4 $\mu$M CaCl$_2$, H$_2$O, pH 7.4 Alternatively, 10% ethanol can be added to this vehicle.

Compound IC$_{50}$
Example 9 30 $\mu$M
Example 11 81 $\mu$M
Example 13 50 $\mu$M Test 2

5 $\mu$M ADP is added in vitro to 50 $\mu$L of vehicle and 400 $\mu$L of platelet rich plasma from Sprague-Dawley rats of either sex that have not been administered any non-steroidal anti-inflammatory drugs for ten days prior to blood-letting. After an ADP-induced platelet aggregation response is seen, 50 $\mu$L of compound is incubated with the aggregated platelets for ninety seconds at 37° C. A compound is rated active if, after three separate incubations, the mean ADP-induced response is reduced by 50% or more. Suitable vehicle for delivery of compound is as stated in Test 1, above.

Compound IC$_{50}$
Example 5 58 μM
Example 6 21 μM
Example 8 23 μM
Example 9 23 μM
Example 10 71 μM
Example 11 43 μM
Example 12 49 μM Test 3

2 μg collagen is added in vitro to 50 μL of vehicle and 400 μL of platelet-rich plasma of Sprague- Dawley rats of either sex that have not been administered any non-steroidal anti-inflammatory drugs for ten days prior to blood-letting. After a collagen-induced platelet aggregation response is seen, 50 μL of compound is incubated with the aggregated platelets for ninety seconds at 37° C. A compound is rated active if, after three separate incubations, the mean collagen-induced response is reduced by 50% or more. Suitable vehicle for delivery of compound is as stated in Test 1, above.

Compound IC$_{50}$
Example 2 21 μM
Example 3 22 μM
Example 4 17 μM
Example 5 58 μM
Example 9 7 μM
Example 10 3.5 μM The results of these studies indicate that the compounds of the invention have anti-aggregation activity in platelets that have been exposed to collagen. As described above, since collagen-induced platelet aggregation can lead to the formation of atherosclerotic plaque formation, the compounds of the invention therefore have utility as anti-thrombotic agents.

The following non-limiting examples further illustrate details for the preparation of the compounds of the invention. Those skilled in the art will readily understand that known variations of the conditions and processes of the final preparative procedures can be used to prepare these compounds. All temperatures are degrees Celsius unless otherwise noted.

EXAMPLE 2

3-(3-chlorophenyl)-5[[(phenylmethyl)thio]methyl]-2-thioxo-4-imidazolidinone.

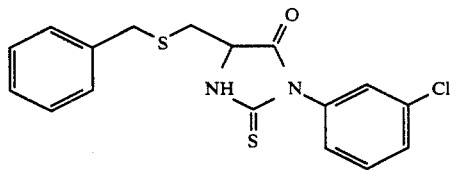

Ten grams of S-benzylcysteine (0.0473 mole) was dissolved in a solution of 100 mL of water containing 1.89 g of NaOH (0.0473 mole). To this solution was added a solution of 8.02 g of 3-m-chlorophenylisothiocyanate in 50 ml of tetrahydrofuran. After the reaction solution was allowed to stand at room temperature for 18 hours, it was acidified with ethylacetate and an excess of an aqueous solution of potassium bisulfate. The aqueous phase was separated and washed with several portions of ethyl acetate. The organic extracts were combined, dried over magnesium sulfate and distilled to dryness under reduced temperature and pressure to yield 22.4 g of crude product as a dark orange oil.

The above crude thiourea was dissolved in 150 ml of tetrahydrofuran and 25 ml of water and 10 ml of concentrated HCl was added to the solution. After several days, 18.2 g of a crude product which precipitated was collected by filtration. It was purified by chromatography on silica gel. Elution of the column with ethyl acetate-methylene chloride (3:7) yielded pure product of the title compound: RF on silica gel=0.33 [ethyl acetate-hexane (3:7)].

EXAMPLE 3

3-phenyl-5S-[[(phenylmethyl)thio]methyl]-2-thioxo-4-imidazolidinone

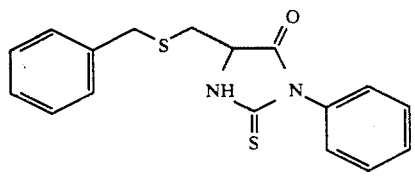

D ENANTIOMER

One-half gram of S-benzyl-D-cysteine (0.00236 mole) was dissolved in a solution of 0.094 g of sodium hydroxide (0.00236 mole) in 50 ml of water. To this solution was then added a solution of 0.32 g of phenylisothiocyanate (0.00236 mole) and tetrahydrofuran. After the mixture was stirred for three hours, it was diluted with 3 ml of concentrated HCl and stirred for another three hours. When the reaction mixture was distilled to dryness under reduced temperature and pressure, it yielded a solid residue which was isolated by decantation and dissolved in isopropyl alcohol. When the isopropyl alcohol solution was removed by distillation at reduced pressure, a white crystalline solid remained. The crude product was purified by chromatography on silica gel. Elution of the column with ethyl acetate-hexane (1:1) yielded pure title compound: RF on silica gel=0.33 [ethyl acetate-hexane (3:7)].

EXAMPLE 4

3-(4-methylphenyl)-5-[[(phenylmethyl)thio]methyl]-2-thioxo-4-imidazolidinone

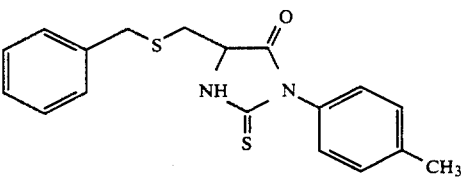

When 10 g of S-benzylcysteine (0.0473 mole), 1.89 g of sodium hydroxide (0.0473 mole) and 7.05 g of p-tolylisothiocyanate (0.0473 mole) was reacted according to the procedure outlined in the preparation of Example 2, 18.1 g of the crude thiourea was obtained and 14.3 g of pure title compound was obtained: RF on silica gel=approximately 0.33 [ethyl acetate-hexane (3:7)].

EXAMPLE 5

5-[[(phenylmethyl)thio]methyl]-2-thioxo-3-[(3-trifluoromethyl)phenyl]-4-imidazolidinone

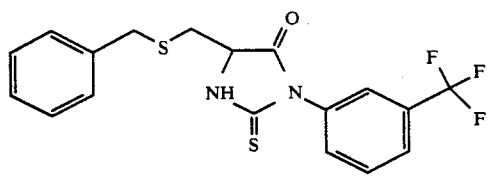

When 10 g of S-benzylcysteine (0.473 mole), 1.92 g of sodium hydroxide (0.0473 mole) and 9.6 g of n-trifluoromethylphenyl isothiocyanate (0.0473 mole) were reacted according to the procedure for the preparation of the title compound of Example 2, 13.4 gram of the title compound for this Example was obtained: RF on silica gel=about 0.25 [ethyl acetate-hexane (3:7)].

EXAMPLE 6

3-phenyl-5-[(2-propenylthio)methyl]-2-thioxo-4-imidazolidinone

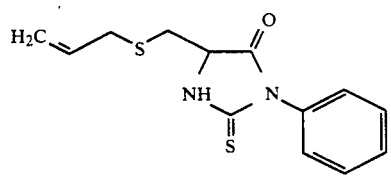

When 5 g of S-allylcysteine (0.031 mole), 1.24 g of sodium hydroxide (0.31 mole) and 4.19 g of phenylisothiocyanate (0.031 mole) were reacted according to the procedure for the preparation of the compound of Example 2, 8.59 g of crude product was obtained which did not require purification by chromatography. Crystallization of the crude product from isopropyl alcohol gave pure title compound: RF on silica gel=0.44 [ethyl acetate-hexane (2:3)].

EXAMPLE 7

5-[[[(4-chlorophenyl)methyl]thio]methyl]-3-phenyl-2-thioxo-4-imidazolidinone.

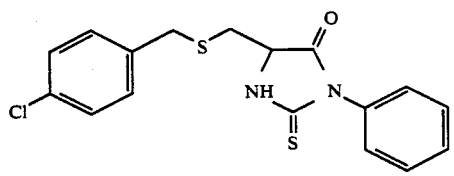

When 10 g of p chlorobenzyl-S cysteine (0.0406 mole), 1.63 g of sodium hydroxide (0.0406 mole) and 5.48 g of phenylisothiocyanate (0.0406 mole) were treated according to the preparation of the product of Example 2, 16.2 g of thiourea and 2.58 g of pure product was obtained: RF on silica gel=0.33 [ethyl acetate-hexane (2:3)].

EXAMPLE 8

3-(phenylmethyl)-5-[[(phenylmethyl)thio]methyl]-2-thioxo-4-imidazolidinone.

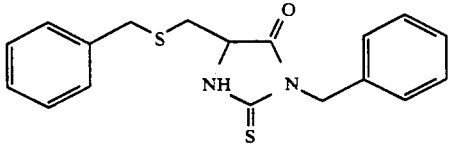

When 2 g of S-benzylcysteine (0.0095 mole), 0.41 g of sodium hydroxide (0.0104 mole) and 1.55 g of benzylisothiocyanate (0.0104 mole) was treated according to the procedure for the preparation of the compound of Example 2, 0.289 g of pure title compound was obtained by crystallization from isopropyl alcohol: ₁H NNR was consistent with the assigned structure for the thiohydantoin.

EXAMPLE 9

3-phenyl-5-[(phenylmethoxy)methyl]-2-thioxo-4-imidazolidinone

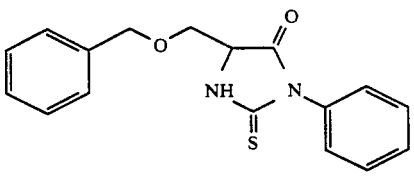

When 3.0 g of O-benzylserine (0.0154 mole), 0.903 g of potassium hydroxide (0.0161 mole), and 2.86 g of benzylisothiocyanate (0.0192 mole) were reacted according to the procedure for the preparation of the compound of Example 2, the title compound was herein obtained.

EXAMPLE 10

3-phenyl-5-[[(phenylmethyl)thio]methyl]-2-thioxo-4-imidazolidinone

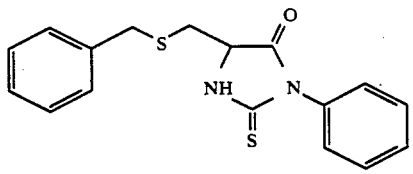

When approximately equimolar amounts of S-benzylcysteine, sodium hydroxide, and phenylisothiocyanate was reacted according to the procedure described for the preparation of the compound of Example 2, the title compound herein was obtained.

When approximately equimolar amounts of 1) sodium hydroxide; 2) a cysteine moiety chosen from the table below; and 3) an isocyanate moiety chosen from the table below are reacted according to the procedure described for the preparation of the compound of example 2, the following compounds are obtained.

| Example | Elementary Analyses (Calculated/Found, respectively) | | |
|---|---|---|---|
| | C | H | N |
| 2 | 56.28/56.32 | 4.13/4.19 | 7.71/7.87 |
| 3 | 62.16/61.40 | 4.87/4.87 | 8.64/8.64 |
| 4 | 63.15/63.18 | 5.25/5.33 | 8.17/8.22 |
| 5 | 54.53/54.67 | 3.81/3.81 | 7.06/7.13 |
| 6 | 56.11/56.39 | 5.03/5.05 | 10.06/9.94 |
| 7 | 56.28/56.22 | 4.13/4.27 | 7.71/7.99 |
| 8 | 63.15/62.80 | 5.25/5.16 | 8.17/8.27 |
| 11 | 56.28/55.36 | 4.13/4.17 | 7.71/7.56 |
| 12 | 60.33/60.08 | 5.02/5.05 | 7.81/7.84 |
| 13 | 59.08/58.75 | 6.10/6.00 | 10.59/10.61 |

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth hereinabove may be applicable as a consequence of variations in the responsiveness of the mammal being treated for severity of platelet aggregation, thrombosis, or atherosclerosis; dosage-related adverse effects, if any; and analogous considerations. Likewise, the specific pharmacological responses observed may vary according to and depending upon the particular active compound selected or whether there are present certain pharmaceutical carriers, as well as the type of formulation and mode of administration employed; and such expected variations or differences in the results are contemplated in accordance with the objects and practices of the present invention. It is intended therefore that the invention be limited only by the scope of the claims which follow and that such claims be interpreted as broadly as is reasonable.

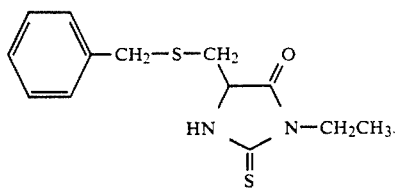

What is claimed is:

1. A compound of the formula

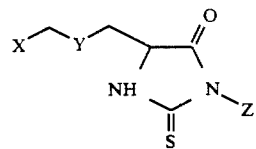

or a pharmaceutically acceptable salt thereof wherein
X is phenyl, halogen substituted phenyl, alkyl of 1 to 5 carbon atoms, alkenyl of 2 to 5 carbon atoms with one or more degrees of unsaturation, or alkynyl of 2 to 5 carbon atoms with one or more degrees of unsaturation;
Y is O or S; and
Z is alkyl of 1 to 5 carbon atoms, phenyl or phenyl substituted by halogen, alkyl of 1 to 5 carbon atoms, alkyloxy of 1 to 5 carbon atoms, halogen substituted alkyl of 1 to 5 carbon atoms, or phenylalkyl of 1 to 5 carbon atoms,
with a proviso that when Z is phenyl, phenyl substituted by halogen or phenylalkyl, and Y is S, X cannot be alkyl, phenyl or halogen substituted phenyl 2. A compound as claimed in claim 1 3-ethyl-5-[[(phenylmethyl)thio]methyl]-2-thioxo-4-imidazolidinone.

3. A compound as claimed in claim 1, wherein X is phenyl.

4. A compound as claimed in claim 1, wherein X is ethylenyl.

5. A compound as claimed in claim 1, wherein X is para-chloro phenyl.

6. A compound as claimed in claim 1, wherein Y is O.

7. A compound as claimed in claim 1, wherein Y is S.

8. A compound as claimed in claim 1, wherein Z is phenyl.

9. A compound as claimed in claim 1, wherein Z is ethyl.

10. A compound as claimed in claim 1, wherein Z is para chloro phenyl.

11. A compound as claimed in claim 1, wherein Z is para-methoxy phenyl.

12. A compound as claimed in claim 1, wherein Z is meta-chloro phenyl.

13. A compound as claimed in claim 1, wherein Z is para-methyl phenyl.

14. A compound as claimed in claim 1, wherein Z is meta-trifluoromethyl.

15. A compound as claimed in claim 1, which has the structural formula

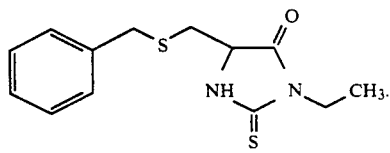

16. A compound as claimed in claim 1, which has the structural formula

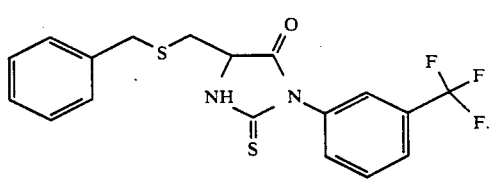

17. A method of inhibiting platelet aggregation in a mammal in need thereof, comprising administering to said mammal a pharmacologically effective amount of a compound according to the general formula

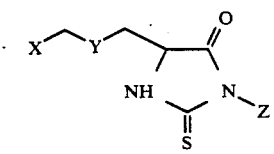

and the pharmaceutically acceptable salts thereof wherein
X is phenyl, halogen substituted phenyl, alkyl of 1 to 5 carbon atoms, alkenyl of 2 to 5 carbon atoms with one or more degrees of unsaturation, or alkynyl of 2 to 5 carbon atoms with one or more degrees of unsaturation;
Y is O or S; and
Z is alkyl of 1 to 5 carbon atoms, phenyl, or phenyl substituted by halogen, alkyl of 1 to 5 carbon atoms, alkyloxy of 1 to 5 carbon atoms, halogen substituted alkyl of 1 to 5 carbon atoms or phenylalkyl of 1 to 5 carbon atoms.

18. The method as claimed in claim 17, in which the compound used has the structural formula

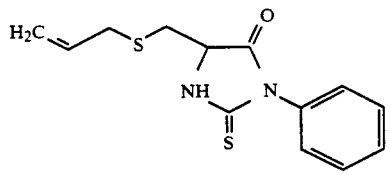

19. The method as claimed in claim 17, in which the compound used has the structural formula

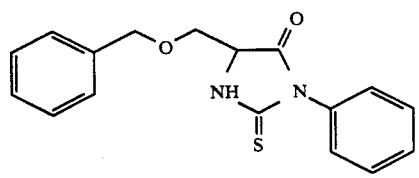

20. The method as claimed in claim 17, in which the compound used has the structural formula

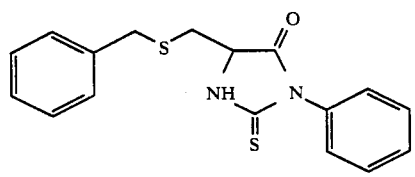

21. The method as claimed in claim 17, in which the compound used is taken from the group consisting of
3-(4-chlorophenyl)-5-[[(phenylmethyl)thio]methyl]-2-thioxo-4-imidazolidinone;
3-(4-methoxyphenyl)-5-[[(phenylmethyl)thio]methyl]-2-thioxo-4-imidazolidinone;
3-phenyl-5S-[[(phenylmethyl)thio]methyl]-2-thioxo-4-imidazolidinone;
3-phenyl-5-[[(phenylmethyl)thio]methyl]-2-thioxo-4-imidazolidinone;
3-(phenylmethyl)-5-[[(phenylmethyl)thio]methyl]-2-thioxo-4-imidazolidinone;
3-phenyl-5-[(phenylmethoxy)methyl]-2-thioxo-4-imidazolidinone;
5-[[(phenylmethyl)thio]methyl]-2-thioxo-3-[(3-trifluoromethyl)phenyl]-4-imidazolidinone;
3-(4-methylphenyl)-5-[[(phenylmethyl)thio]methyl]-2-thioxo-4-imidazolidinone;
5-[[[(4-chlorophenyl)methyl]thio]methyl]-3-phenyl-2-thioxo-4-imidazolidinone;
3-(3-chlorophenyl)-5-[[(phenylmethyl)thio]methyl]-2-thioxo-4-imidazolidinone;

3-ethyl-5-[[(phenylmethyl)thio]methyl]-2-thioxo-4-imidazolidinone; and 3-phenyl-5-[(2-propenylthio)methyl]-2-thioxo-4-imidazolidinone.

22. A pharmaceutical composition useful for inhibiting platelet aggregation comprising an effective amount of at least one compound according to claim 1, together with one or more non-toxic pharmaceutically acceptable carrier.

23. The method as claimed in claim 17, in which the compound used has the structural formula